United States Patent
Curtze et al.

[11] Patent Number: 5,945,567
[45] Date of Patent: Aug. 31, 1999

[54] FUNGICIDAL 2-METHOXYBENZOPHENONES

[75] Inventors: Juergen Curtze, Geisenheim; Werner Simon, Hueffelsheim; Gerd Morschhaeuser, Gau-Algesheim; Andreas Waldeck, Heidesheim; Karl-Otto Stumm, Aspisheim; Henry Van Tuyl Cotter, Ingelheim; Guido Albert, Hackenheim; Annerose Rehnig, Ingelheim; Gunther Reichert, Bubenheim, all of Germany

[73] Assignee: American Cyanamid Company, Madison, N.J.

[21] Appl. No.: 08/914,966

[22] Filed: Aug. 20, 1997

[51] Int. Cl.⁶ .......................... C07C 49/24; A61K 31/12
[52] U.S. Cl. ............................... 568/333; 514/687
[58] Field of Search ............... 568/333; 514/687

[56] References Cited

FOREIGN PATENT DOCUMENTS

0727141 A2  8/1996  European Pat. Off. ....... A01N 35/04

OTHER PUBLICATIONS

Hendrickson et al, Organic Chemistry, third edition, pp. 414–415, 1970.
Harrison et al, Compendium of Organic Synthetic Methods,, pp. 320–322, 1971.

Primary Examiner—Gary Geist
Assistant Examiner—Sreeni Padmanabhan
Attorney, Agent, or Firm—Gregory M. Hill

[57] ABSTRACT

Substituted benzophenone compounds are disclosed, having the formula:

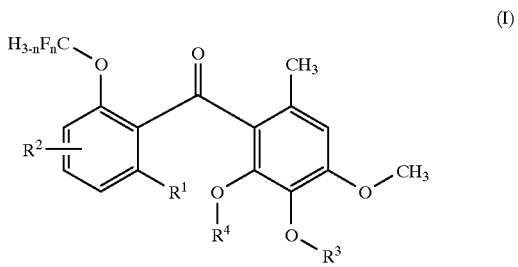

The compounds are useful as fungicides having high systemicities.

13 Claims, No Drawings

FUNGICIDAL 2-METHOXYBENZOPHENONES

BACKGROUND OF THE INVENTION

This invention relates to certain benzophenone compounds, a process for their preparation, compositions containing such compounds, a method for combating a fungus at a locus comprising treating the locus with such compounds and their use as fungicides.

Food production relies upon a variety of agricultural technologies to ensure the growing population's dietary needs remain affordable, nutritious and readily available on grocery store shelves. Fungicides are one of these agricultural technologies which are available to the world community. Fungicides are agrochemical compounds which protect crops and foods from fungus and fungal diseases. Crops and food are constantly threatened by a variety of fungal organisms, which, if left uncontrolled, can cause ruined crops and devastated harvests.

In particular, ascomycetes, the causative agent for powdery mildew diseases are an ever-present threat especially to cereal and fruit crops. However, applications of fungicidal agents at disease control rates can cause phytotoxic damage to the target plants.

The compounds of the present invention are disclosed in a general formula of European patent ("EP") application EP 0 727 141, which published on Aug. 21, 1996. The EP application discloses compounds having activity against phytopathogenic fungi, but relatively low systemicity.

There is no disclosure in the EP application of substituted benzophenones, wherein the first phenyl group is substituted by a methoxy group in the 2-position and by a halogen atom or an alkyl group in the 6-position and the second phenyl group is substituted by three alkoxy groups and one methyl group.

SUMMARY OF THE INVENTION

The present invention provides a compound of formula I

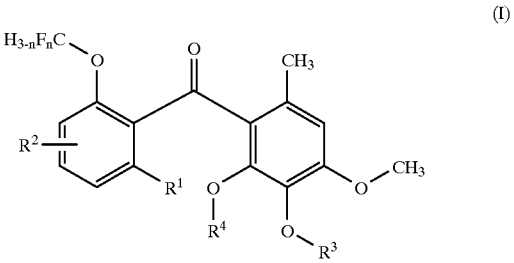

(I)

wherein
  $R^1$ represents a halogen atom or an alkyl group;
  $R^2$ represents a hydrogen or halogen atom, or an alkyl, alkoxy or nitro group; or $R^1$ and $R^2$ together represent a group of formula —CH=CH—CH=CH—;
  $R^3$ and $R^4$ each independently represent an optionally substituted alkyl group; and
  n is an integer from 0 to 3.

The compounds combine relatively excellent selective fungicidal activities in various crops with comparably high systemicities.

It is an object of the present invention to provide highly systemic fungicidal compounds.

It is also an object of the invention to provide methods for controlling an undesired fungus by contacting said plants with a fungicidally effective amount of the compounds.

It is another object of the invention to provide selective fungicidal compositions containing the compounds as active ingredients.

These and other objects and features of the invention will be more apparent from the detailed description set forth hereinbelow, and from the appended claims.

DETAILED DESCRIPTION OF THE PREFERRED EMBODIMENTS

It has surprisingly been found that the compounds of formula I

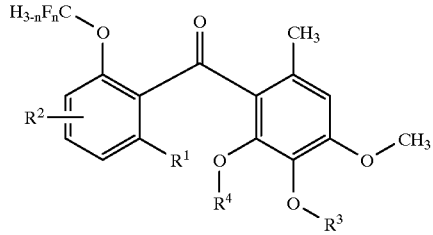

(I)

in which $R^1$ through $R^4$ and n have the meaning given above combine relatively excellent fungicidal activity against phytopathogenic fungi, in particular those that cause powdery mildew diseases and have comparably high systemicity.

In general terms, unless otherwise stated, as used herein the term halogen atom may denote a bromine, iodine, chlorine or fluorine atom, and is especially a bromine, chlorine or fluorine atom, in particular a bromine or chlorine atom.

Optionally substituted moieties may be unsubstituted or have from one up to the maximal possible number of substituents. Typically, 0 to 2 substituents are present. Each optionally substituted group independently is substituted by one or more halogen atoms or nitro, cyano, cycloalkyl, preferably $C_{3-6}$ cycloalkyl, cycloalkenyl, preferably $C_{3-6}$ cycloalkenyl, haloalkyl, preferably $C_{1-6}$ haloalkyl, halocycloalkyl, preferably $C_{3-6}$ halocycloalkyl, alkoxy, preferably $C_{1-6}$ alkoxy, haloalkoxy, preferably $C_{1-6}$ haloalkoxy, phenyl, halo- or dihalo-phenyl or pyridyl groups.

In general terms, unless otherwise stated herein, the terms alkyl and alkoxy as used herein with respect to a radical or moiety refer to a straight or branched chain radical or moiety. As a rule, such radicals have up to 10, in particular up to 6 carbon atoms. Suitably an alkyl or alkoxy moiety has from 1 to 6 carbon atoms, preferably from 1 to 5 carbon atoms. A preferred alkyl moiety is the methyl, ethyl, n-propyl, isopropyl or n-butyl group.

The invention especially relates to compounds of the general formula I in which any alkyl part of the groups $R^1$ through $R^4$, which may be straight chained or branched, contains up to 10 carbon atoms, preferably up to 9 carbon atoms, more preferably up to 6 carbon atoms, and in which each optionally substituted group independently is substituted by one or more halogen atoms or nitro, cyano, cycloalkyl, preferably $C_{3-6}$ cycloalkyl, cycloalkenyl, preferably $C_{3-6}$ cycloalkenyl, haloalkyl, preferably $C_{1-6}$ haloalkyl, halocycloalkyl, preferably $C_{3-6}$ halocycloalkyl, alkoxy, preferably $C_{1-6}$ alkoxy, haloalkoxy, preferably $C_{1-6}$ haloalkoxy, phenyl, or pyridyl groups, in which the phenyl moiety is optionally substituted by one or two substituents selected from halogen atoms, cyano, $C_{1-6}$ alkyl and $C_{1-6}$ alkoxy groups.

The invention especially relates to compounds of the general formula I in which $R^1$ represents a halogen atom, in particular chlorine, a straight-chained or branched $C_{1-10}$ alkyl, in particular a straight-chained $C_{1-3}$ alkyl group, most preferably being a methyl group.

The invention especially relates to compounds of the general formula I in which $R^2$ represents a hydrogen or halogen atom, in particular a chlorine, bromine or iodine atom, a nitro, a $C_{1-10}$ alkyl or a $C_{1-10}$ haloalkyl group, most preferred being a hydrogen, chlorine or bromine atom. If $R^2$ is different from hydrogen, it is most preferred attached in the ortho-position to radical $R^1$.

The invention especially relates to compounds of the general formula I in which $R^3$ and $R^4$ each independently represent an optionally substituted straight-chained or branched $C_{1-5}$ alkyl, in particular a straight-chained $C_{1-3}$ alkyl group, most preferably an unsubstituted or substituted methyl group. This methyl group is preferably unsubstituted or substituted by a phenyl group which is unsubstituted or substituted by one to five, preferably one or two halogen atoms or $C_{1-4}$ alkyl or $C_{1-4}$ alkoxy groups.

The benzophenone compounds according to formula I are oils, gums, or crystalline solid materials and possess valuable fungicidal properties. For example, they can be used in agriculture, or related fields such as horticulture and viticulture, for the control of phytopathogenic fungi, especially ascomycetes, in particular powdery mildew diseases such as those caused by *Erysiphe graminis, Podosphaera leucotricha, Uncinula necator* and the like. Said benzophenone compounds possess a high fungicidal activity over a wide concentration range and may be used in agriculture without harmful phytotoxic effects.

Moreover, the compounds according to the invention show enhanced curative and residual control of fungi and fungal diseases such as cereal, cucumber and grape powdery mildew, and improved foliar systemicity compared with conventional fungicides.

Useful results in terms of control of phythopathogenic fungi are obtained with a compound as defined in formula I wherein:

$R^1$ represents a chloro atom or a methyl group;
$R^2$ represents a hydrogen, chloro or bromo atom;
$R^3$ represents a $C_{1-5}$ alkyl group;
$R^4$ represents a $C_{1-5}$ alkyl group or a benzyl group being optionally substituted by one or more halogen atoms or one or more $C_{1-4}$ alkyl or alkoxy groups; and
n is 0 or 2, in particular 0.

If $R^2$ represents Cl or Br, it is preferably attached to the benzene ring in the ortho-position with respect to radical $R^1$.

In particular the compounds of formula IA are preferred:

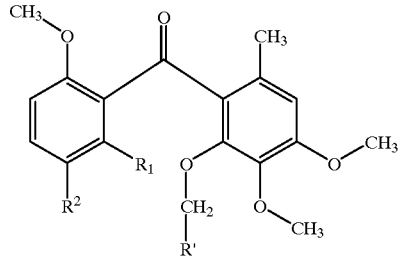

(IA)

in which
$R^1$ represents a chloro atom or a methyl group,
$R^2$ represents a hydrogen, chloro or bromo atom or a methyl group, and
R' represents a hydrogen atom or a $C_{1-4}$ alkyl or a phenyl group being optionally substituted by one or more fluorine atoms or one or more $C_{1-4}$ alkyl groups.

In particular the compounds of formula IB are preferred:

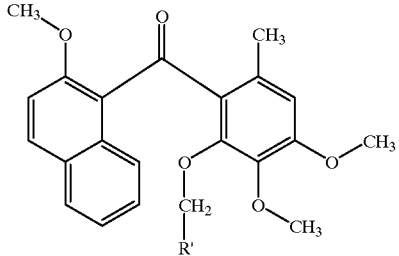

(IB)

in which
R' represents a hydrogen atom or a $C_{1-4}$ alkyl or a phenyl group being optionally substituted by one or more fluorine atoms or one or more $C_{1-4}$ alkyl groups.

Especially good results in terms of control of phytopathogenic fungi are obtained by using, for example, the following compounds of formula I:

6,6'-dimethyl-2,2',3',4'-tetramethoxy-benzophenone,
6,6'-dimethyl-3'-pentoxy-2,2',4'-trimethoxy-benzophenone,
5-bromo-6,6'-dimethyl-2,2',3',4'-tetramethoxy-benzophenone,
5-chloro-6,6'-dimethyl-2,2',3',4'-tetramethoxy-benzophenone,
5-iodo-6,6'-dimethyl-2,2',3',4'-tetramethoxy-benzophenone,
6-chloro-6'-methyl-2,2',3',4'-tetramethoxy-benzophenone,
5-bromo-6-chloro-6'-methyl-2,2',3',4'-tetramethoxy-benzophenone,
6-chloro-5,6'-dimethyl-2,2',3',4'-tetramethoxy-benzophenone,
2'-n-butoxy-6-chloro-6'-methyl-2,3',4'-trimethoxy-benzophenone,
2'-n-butoxy-6-chloro-5,6'-dimethyl-2,2',3'-trimethoxy-benzophenone
6-chloro-2'-(2-fluorobenzyloxy)-6'-methyl-2,3',4'-trimethoxy-benzophenone,
6-chloro-2'-(4-fluorobenzyloxy)-6'-methyl-2,3',4'-trimethoxy-benzophenone,
5-bromo-6,6'-dimethyl-3'-n-pentyloxy-2,2',4'-trimethoxy-benzophenone
6-chloro-6'-methyl-2'-n-pentyloxy-2,3',4'-trimethoxy-benzophenone,
6-chloro-2'-(3-methylbutyloxy)-6'-methy-2,3',4'-trimethoxy-benzophenone,
2'-benzyloxy-6-chloro-6'-methyl-2,3',4'-trimethoxy-benzophenone,
6-chloro-2'-(3-methylbenzyloxy)-6'-methyl-2,3',4'-trimethoxy-benzophenone,
6-chloro-2'-(4-methylbenzyloxy)-6'-methyl-2,3',4'-trimethoxy-benzophenone,
6-chloro-2-difluoromethoxy-6'-methyl-2',3',4'-trimethoxy-benzophenone,
1-(6-methyl-2,3,4-trimethoxybenzoyl)-2-methoxynaphthalene,
1-(6-methyl-2,3,4-trimethoxybenzoyl)-2-difluoromethoxynaphthalene.

The present invention further provides a process (A) for the preparation of a compound of formula I, wherein n is 0, which comprises treating a compound of the general formula II (a) reacting a compound of formula VI,

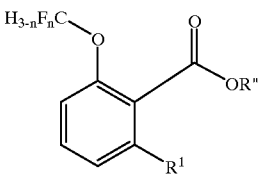

(II)

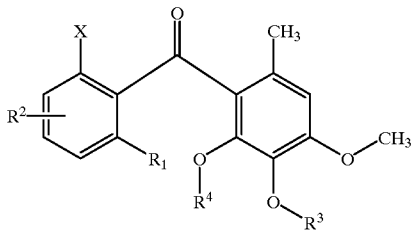

wherein $R^1$, $R^2$, $R^3$ and $R^4$ have the meaning given above and X represents a fluoro or chloro atom, with an alkali methylate, preferably sodium methylate.

Another possibility for the preparation of the compounds of formula I is a process (B) which comprises the steps of (a) reacting a compound of formula III,

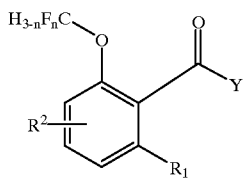

(III)

wherein $R^1$, $R^2$ and n have the meaning given above and Y represents a leaving group, in particular a chloro atom or a hydroxy group, with compound of formula IV,

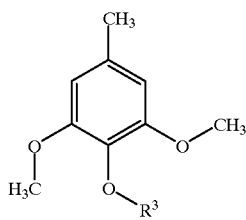

(IV)

wherein $R^3$ has the meaning given for claim 1; in the presence of a Lewis acid (Y=leaving group) or a dehydrating agent (Y=OH), preferably phosphorous pentoxide or $POCl_3$; and (b) optionally treating the resulting benzophenone of formula I, wherein $R^4$ represents a methyl group, with a compound of formula V,

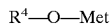

$R^4$—O—Met (V)

wherein $R^4$ represents an optionally substituted alkyl group, being different from methyl, and Met denotes an alkali metal atom, preferably sodium.

The compounds of formula III, wherein $R^2$ represents a halogen atom, are preferably obtained by a process (C) which comprises the steps of (VI)

wherein $R^1$ and n have the meaning given for claim 1 and R" represents a hydrogen atom or an alkyl group, with a halogenating agent, (b) optionally hydrolyzing the resulting halogenated alkyl benzoate (R"=alkyl), and (c) optionally treating the resulting halogenated benzoic acid with thionyl chloride.

The starting materials of formula II, III, IV, V and VI are known products, and may themselves be prepared according to established methods or routine adaptations thereof. Substituents which are not compatible with the selected reaction conditions may be introduced after formation of the benzophenone. They may be generated by known methods such as subsequent derivatization or substitution of a suitable group or by cleaving off a suitable protecting group.

The reaction between the 2-halobenzophenone of formula II and the alkali metal methylate is preferably carried out in the presence of a solvent, such as ethers like tetrahydrofuran, diethylether, tert-butyl-methylether or dimethoxyethane or methanol or in mixtures of these solvents. The molar ratio between formula II and the alkali metal methylate is preferably in the range of 0.3 to 1.9 at a temperature between 25 and 120° C.

The Friedel Crafts reaction between formula III and IV is effected in the presence of a Lewis acid catalyst according to well-established procedures (Y=Cl). Suitable catalysts include $FeCl_3$, $AlCl_3$, $SnCl_4$, $ZnCl_2$, $TiCl_4$, $SbCl_5$ and $BF_3$, which may be in a molar equivalent amount (based on the benzoyl chloride of formula III). However, it is also possible to use lesser amounts of catalyst at elevated temperatures, suitably under reflux temperatures, preferred catalysts under these conditions being $FeCl_3$, $I_2$, $ZnCl_2$, iron, copper, strong sulphonic acids such as $F_3CSO_3H$, and acidic ion exchange resins such as Amberlyst® 15 and Nafion®. The preferred catalyst is $FeCl_3$ in a 0.001 to 0.2 molar ratio at a temperature of about 50 to 180° C. The reaction can be carried out in a solvent inert under the reaction conditions, for example ethylene or methylene chloride, benzene, octane, decane or solvent mixtures, or in the absence of solvent, conveniently by employing one of the reactants in excess, e. g. in the range of 1:5 to 5:1. If $AlCl_3$ is being used, the molar ratio is preferably in the range of 0.5 to 2 and the suitable solvents are e.g. methylenechloride or ethylenechloride at a temperature usually between –10 and 70° C.

In another preferred process according to the invention the benzoic acid of formula III (Y=OH) is reacted with a compound of formula IV in the presence of phosphorous pentoxide at temperatures of about 0 to 50° C., preferably at room temperature or in the presence of $POCl_3$ at temperatures of about 50 to 150° C., preferably under reflux.

The halogenation of the benzoate of formula VI is preferably carried out in the presence of an inert solvent. Preferred halogenating agents are for example sulfuryl chloride, bromine and N-iodo-succinimide. If $R^1$ represents a halogen atom highly polar solvents such as alcohols or carboxylic acids, in particular acetic acid are preferred. If $R^1$ represents an alkyl group, in particular a methyl group, apolar solvents such as tetrachloromethane are preferred. If the reaction is carried out with bromine at a temperature between 0 and 40° C., preferably at room temperature, the halogenation takes place predominately in the orthoposition with respect to radical $R^1$.

The reaction between the benzophenones of formula I, wherein $R^4$ represents a methyl group and the alkali metal alkoxides of formula V is preferably carried out in the presence of a solvent, such as ethers like tetrahydrofuran, diethylether, tert-butyl-methylether or dimethoxyethane or an alcohol of formula $R^4$—OH, in which $R^4$ is different from methyl, or in mixtures of these solvents. The molar ratio between formula II and the alkali metal alkoxide is preferably in the range of 0.3 to 1.9 at a temperature between 25 and 120° C.

The processes described below can analogously be applied to other starting compounds, if desired.

Due to excellent plant tolerance, the compounds of formula I may be used in cultivation of all plants where infection by the controlled fungi is not desired, e.g. cereals, vegetables, legumes, apples, vine. The absence of target crop phytotoxicity at fungus control rates is a feature of the present invention.

Accordingly the invention further provides a fungicidal composition which comprises a carrier and, as active ingredient, at least one compound of formula I as defined above. A method of making such a composition is also provided which comprises bringing a compound of formula I as defined above into association with at least one carrier. Such a composition may contain a single compound or a mixture of several compounds of the present invention. It is also envisaged that different isomers or mixtures of isomers may have different levels or spectra of activity and thus compositions may comprise individual isomers or mixtures of isomers.

A composition according to the invention preferably contains from 0.5% to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including material which is normally gaseous but which has been compressed to form a liquid, and any of the carriers normally used in formulating fungicidal compositions may be used.

The compositions may be manufactured into e.g. emulsion concentrates, solutions which may be sprayed directly or diluted, diluted emulsions, wettable powders, soluble powders, dusts, granulates, waterdispersible granulates, microencapsulates by well-established procedures. The form of application such as spraying, atomizing, dispersing, pouring may be chosen like the compositions according to the desired objectives and the given circumstances.

The formulations, i.e. the compositions which comprise at least one compound according to general formula I and optionally solid and/or liquid auxiliaries and adjuvants, may be prepared by well-established procedures, e.g. intensive mixing and/or grinding of the active ingredients with other substances, such as fillers, solvents, solid carriers, and optionally surface-active compounds or adjuvants.

Solvents may be aromatic hydrocarbons, preferably the fractions $C_8$ to $C_{12}$, e.g. xylenes or xylene mixtures, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, dimethyl sulphoxide, alkyl formamides, epoxidized vegetable oils, e.g. epoxidized coconut or soybean oil, water. Mixtures of different liquids are often suitable.

Solid carriers, which may be used for dusts or dispergible powders, may be mineral fillers, such as calcite, talc, kaolin, montmorillonite, attapulgite. The physical properties may be improved by addition of highly dispersed silica gel or highly dispersed polymers. Carriers for granulates may be porous material, e.g. pumice, broken brick, sepiolite, bentonite, non-sorptive carriers may be calcite or sand. Additionally, a multitude of pre-granulated inorganic or organic materials may be used, such as dolomite or crushed plant residues.

Fungicidal compositions are often formulated and transported in concentrated form which is subsequently diluted by the user before application. The presence of small amounts of a carrier which is a surface-active agent facilitates this process of dilution. Thus, preferably one carrier in a composition according to the invention is a surface active agent. For example, the composition may contain at least two carriers, at least one of which is a surface active agent.

Suitable surface-active substances may be non-ionogenic, anionic or cationic surfactants with good dispersing, emulgating and wetting properties depending on the nature of the compound according to general formula I to be formulated. Surfactants may also mean mixtures of surfactants.

Suitable surfactants may be so-called water-soluble soaps as well as water-soluble synthetic surface-active compounds.

Soaps usually are alkali, earth alkali or optionally-substituted ammonium salts of higher fatty acids ($C_{10}$–$C_{20}$), e.g. the sodium or potassium salts of oleic or stearic acid or of mixtures of natural fatty acids which are prepared, for example, from coconut or tallow oil. Furthermore, methyl-taurine salts of fatty acids may be used.

However, so-called synthetic surfactants are preferably used, especially fatty sulphonates, fatty sulphates, sulphonated benzimidazole derivatives or alkyl aryl sulphonates.

The fatty sulphates or fatty sulphonates are normally used as alkali, earth alkali or optionally-substituted ammonium salts and have an alkyl moiety of 8 to 22 carbon atoms, whereby alkyl also means the alkyl moiety of acyl residues, such as the sodium or calcium salt of lignin sulphonic acid, of sulphuric acid dodecylate or of a mixture of fatty alcohols prepared from natural fatty acids. This also includes the salts of sulphuric acid esters, sulphonic acids and adducts of fatty alcohols and ethylene oxide. The sulphonated benzimidazole derivatives preferably contain 2 sulphonic acid residues and a fatty acid residue with 8 to 22 carbon atoms. Alkyl aryl sulphonates are, for example, the sodium, calcium or triethyl ammonium salts of dodecyl benzene sulphonic acid, dibutyl naphthalene sulphonic acid or of a condensate of naphthalene sulphonic acid and formaldehyde.

Furthermore, phosphates, such as the salts of the phosphoric acid ester of a p-nonylphenol-(4–14)-ethylene oxide adduct or phospholipids, may be used.

Non-ionic surfactants are preferably polyglycolether derivatives of aliphatic or cycloaliphatic alcohols, saturated or non-saturated fatty acids and alkylphenols, which have 3 to 10 glycol ether groups and 8 to 20 carbon atoms in the (aliphatic) hydrocarbon residue and 6 to 18 carbon atoms in the alkyl residue of the alkyl phenols.

Other suitable non-ionic surfactants are the water-soluble, 20 to 250 ethylene glycol ether groups containing polyadducts of ethylene oxide and polypropylene glycol, ethylene diamino polypropylene glycol and alkyl polypropylene glycol with 1 to 10 carbon atoms in the alkyl moiety, the substances normally contain 1 to 5 ethylene glycol units per propylene glycol unit.

Examples of non-ionic surfactants are nonylphenol polyethoxy ethanols, castor oil polyglycol ether, polyadducts of ethylene oxide and polypropylene, tributyl phenoxy polyethoxy ethanol, polyethylene glycol, octyl phenoxy polyethoxy ethanol.

Furthermore, fatty acid esters of polyoxy ethylene sorbitan, such as polyoxy ethylene sorbitan trioleate may be used.

Cationic surfactants preferably are quaternary ammonium salts, which have at least one alkyl residue with 8 to 22 carbon atoms and, furthermore, low, optionally-halogenated alkyl, benzyl or hydroxyalkyl residues. The salts are preferably halides, methyl sulphates or alkyl sulphates, e.g. stearyl trimethyl ammonium chloride or benzyl bis(2-chloroethyl) ethyl ammonium bromide.

The compositions of the invention may for example be formulated as wettable powders, dusts, granules, solutions, emulsifiable concentrates emulsions, suspension concentrates and aerosols. Wettable powders usually contain 25%, 50% or 75% w/w of active ingredient and usually contain in addition to solid inert carrier, 3%–10% w/w of a dispersing agent and, where necessary, 0%–10% w/w of stabiliser(s) and/or other additives such as penetrants or stickers. Dusts are usually formulated as a dust concentrate having a similar composition to that of a wettable powder but without a dispersant, and may be diluted in the field with further solid carrier to give a composition usually containing 0.5%–10% w/w of active ingredient. Granules are usually prepared to have a size between 10 and 100 mesh ASTM (approx. 2.00 mm–0.15 mm), and may be manufactured by agglomeration or impregnation techniques. Generally, granules will contain 0.5%–75% active ingredient and 0–10% w/w of additives such as stabiliser, surfactants, slow release modifiers and binding agents. The so called "dry flowable powders" consist of relatively small granules having a relatively high concentration of active ingredient. Emulsifiable concentrates usually contain, in addition to a solvent or a mixture of solvents, 1%–50% w/v active ingredient, 2%–20% w/v emulsifiers and 0%–20% w/v of other additives such as stabilisers, penetrants and corrosion inhibitors. Suspension concentrates are usually compounded so as to obtain a stable, nonsedimenting flowable product and usually contain 10%–75% w/w active ingredient, 0.5%–15% w/w of dispersing agents, 0.1%–10% w/w of suspending agents such as protective colloids and thixotropic agents, 0%–10% of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise' like consistency.

The composition of the invention may also contain other ingredients, for example other compounds possessing herbicidal, insecticidal or fungicidal properties.

Of particular interest in enhancing the duration of the protective activity of the compounds of this invention is the use of a carrier which will provide slow release of the fungicidal compounds into the environment of a plant which is to be protected. Such slow-release formulations could, for example, be inserted in the soil adjacent to the roots of a plant, or could include an adhesive component enabling them to be applied directly to the stem of a plant.

As commodity the compositions may preferably be in a concentrated form whereas the end-user generally employs diluted compositions. The compositions may be diluted to a concentration of 0.001% of active ingredient (a.i.). The doses usually are in the range from 0.01 to 10 kg a.i./ha.

The compositions of this invention can comprise also other compounds having biological activity, e.g. compounds having similar or complementary fungicidal activity or compounds having plant growth regulating, herbicidal or insecticidal activity.

The other fungicidal compound can be, for example, one which is capable of combating diseases of cereals (e.g. wheat) such as those caused by Erysipha, Puccinia, Septoria, Gibberella and Helminthosporium spp., seed and soil borne diseases and downy and powdery mildews on vines and powdery mildew and scab on apples etc. These mixtures of fungicides can have a broader spectrum of activity than the compound of general formula I alone.

Examples of the other fungicidal compound are carbendazim, benomyl, thiophanate-methyl, thiabendazole, fuberidazole, etridiazole, dichlofluanid, cymoxanil, oxadixyl, ofurace, metalaxyl, furalaxyl, benalaxyl, fosetyl-aluminium, fenarimol, iprodione, procymidione, vinclozolin, penconazole, myclobutanil, R0151297, S3308, pyrazophos, ethirimol, ditalimfos, tridemorph, triforine, nuarimol, triazbutyl, guazatine, triacetate salt of 1,1'-iminodi (octamethylene)-diguanidine, propiconazole, prochloraz, flutriafol, hexaconazole, flusilazole, triadimefon, triadimenol, diclobutrazol, fenpropimorph, pyrifenox, cyproconazole, tebuconazole, epoxiconazole, 4-chloro-N-(cyano(ethoxy)methyl)benzamide, fenpropidin, chlorozolinate, diniconazol, imazalil, fenfuram, carboxin, oxycarboxin, methfuroxam, dodemorph, blasticidin S, kasugamycin, edifenphos, kitazin P, cycloheximide, phthalide, probenazole, isoprothiolane, tricyclazole, pyroquilon, chlorbenzthiazon, neoasozin, polyoxin D, validamycin A, mepronil, flutolanil, pencycuron, diclomezin, phenazineoxide, nickel dimethyldithiocarbamate, techlofthalam, bitertanol, bupirimate, etaconazole, streptomycin, cypofuram, biloxazol, quinomethionate, dimethirimol, 1-(2-cyano-2-methoxyimino-acetyl)-3-ethyl urea, fenapanil, tolclofosmethyl, pyroxyfur, polyram, maneb, mancozeb, captafol, chlorothalonil, anilazin, thiram, captan, folpet, zineb, propineb, sulfur, dinocap, binapacryl, nitrothalisopropyl, dodine, dithianon, fentin hydroxide, fentin acetate, tecnazene, quintozen, dichloran, copper-containing compounds such as copper oxychloride, copper sulfate and Bordeaux mixture as well as organic mercury compounds, kresoxim-methyl, azoxystrobin, SSF-126, pyrimethanil, cyprodinil, spiroxamine, fludioxonil, quinoxyfen, carpropamid, metconazole, dimethomorph, famoxadone, propanocarb, flumetover, fenpiclonil, fluazinam, mepanipyrim, triazoxide, chlorothalonil.

In addition, the co-formulations according to the invention may contain at least one benzophenone of formula I and any of the following classes of biological control agents such as viruses, bacteria, nematodes, fungi, and other microorganisms which are suitable to control insects, weeds or plant diseases or to induce host resisitance in the plants. Examples of such biological control agents are: *Bacillus thuringiensis, Verticillium lecanii, Autographica californica NPV, Beauvaria bassiana, Ampelomyces quisqualis, Bacilis*

*subtilis, Pseudomonas fluorescens, Steptomyces griseoviridis* and *Trichoderma harzianum*.

Moreover, the co-formulations according to the invention may contain at least one benzophenone of formula I and a chemical agent that induces the systemic acquired resistance in plants such as for example nicotinic acid or derivatives thereof or BION.

The compounds of general formula I can be mixed with soil, peat or other rooting media for the protection of the plants against seed-borne, soil-borne or foliar fungal diseases.

The invention still further provides the use as a fungicide of a compound of the general formula I as defined above or a composition as defined above, and a method for combating fungus at a locus, which comprises treating the locus, which may be for example plants subject to or subjected to fungal attack, seeds of such plants or the medium in which such plants are growing or are to be grown, with such a compound or composition.

The present invention is of wide applicability in the protection of crop and ornamental plants against fungal attack. Typical crops which may be protected include vines, grain crops such as wheat and barley, rice, sugar beet, top fruit, peanuts, potatoes, vegetables and tomatoes. The duration of the protection is normally dependent on the individual compound selected, and also a variety of external factors, such as climate, whose impact is normally mitigated by the use of a suitable formulation.

The following examples further illustrate the present invention. It should be understood, however, that the invention is not limited solely to the particular examples given below.

EXAMPLE 1

Preparation of 6,6'-dimethyl-2,2',3',4'-tetramethoxy-benzophenone 1A 2-Methoxy-6-methylbenzoic acid A mixture of ethyl 2-methoxy-6-methylbenzoate (5.0 g, 25 mmol), water (10 ml), methanol (40 ml) and sodium hydroxide (2.1 g, 50 mmol) is heated under reflux with stirring. The reaction mixture is diluted with water (150 ml) and acidified with concentrated hydrochloric acid. The solid material is collected by filtration, washed with water and dried yielding dark yellow crystals, 2.1 g, mp 136° C.

1B 2-Methoxy-6-methylbenzoyl chloride

A mixture of 1A (1.7 g, 10.2 mmol) and thionyl chloride (2 ml) is heated under reflux for 1 hour. The mixture is concentrated and the resulting benzoylchloride is used without further purification.

1C 6,6'-dimethyl-2,2',3',4'-tetramethoxy-benzophenone

A mixture of 3,4,5-trimethoxytoluene (1.86 g; 10.2 mmol), 1B (10.2 mmol), aluminium chloride (1.33 g, 10 mmol) and dichloromethane (20 ml) is stirred at 0° C. Subsequently, the reaction mixture is stirred for another 4 hours at room temperature. A mixture of dilute hydrochloric acid and ethyl acetate (1:1 v/v; 100 ml) is then slowly added at 0° C. The organic phase is concentrated and the residue is recrystallized from methanol. The solid material is collected by vacuum filtration, three times washed with methanol/water (3:1 v/v; 100 ml each) and dried yielding white crystals, 1.0 g (30.3%), mp 84° C.

EXAMPLE 2

Preparation of 6,6'-dimethyl-2'-n-butoxy-2,3',4'-trimethoxy-benzophenone

A mixture of n-butanol (5 ml) and sodium hydride (60% in oil, 10 mmol) is stirred until the formation of $H_2$ gas ceases. A mixture of 1C (0.7 g, 2,2 mmol) and dimethoxyethane (15 ml) is added to the resulting reaction mixture. Subsequently, the reaction mixture is heated under reflux with stirring for 24 hours. A mixture of water and ethyl acetate (1:1 v/v; 100 ml) is then slowly added at room temperature. The organic phase is separated, concentrated and the residue is purified by column chromatography (petrol ether:ethyl acetate, 95:5 v/v) yielding the pure product as a yellow oil, 0.2 g, (24.4%).

EXAMPLE 3

Preparation of 6-chloro-2'-pentyloxy-6'-methyl-2,3',4'-trimethoxy-benzophenone

A mixture of sodium methylate in methanol (5.4 mol/l, 19.6 mmol), 2,6-dichloro-3',4'-dimethoxy-6'-methyl-2'-pentyloxy-benzophenone (obtained according to EP 0 727 141, 2.69 g, 6.5 mmol) and dimethoxyethane (20 ml) is heated to 80° C. with stirring for 24 hours. A mixture of water and ethyl acetate (1:1 v/v; 100 ml) is then slowly added at room temperature. The organic phase is separated and concentrated and the residue is purified by column chromatography (dichloromethane) yielding the pure product as a yellow oil, 0.52 g, (19.7%).

EXAMPLE 4

Preparation of 5-bromo-6-chloro-6'-methyl-2,2'3',4'-tetramethoxy-benzophenone

4A Ethyl 5-bromo-6-chloro-2-methoxybenzoate

A mixture of ethyl 6-chloro-2-methoxybenzoate (1.8 g, 8.4 mmol), bromine (1.41 g, 8.8 mmol) and acetic acid (5 ml) is stirred at room temperature for 24 hours. The reaction mixture is poured into water and extracted with ethyl acetate. The organic phase is separated and concentrated and the residue is purified by column chromatography (petrol ether: ethyl acetate, 95:5 v/v) yielding the pure product as a yellow oil, 1.7 g, (69%).

4B 5-Bromo-6-chloro-2-methoxybenzoic acid

A mixture of 4A (1.7 g, 5.8 mmol), water (10 ml), ethanol (20 ml) and sodium hydroxide (0.5 g, 12.5 mmol) is heated under reflux with stirring. The reaction mixture is diluted with water (80 ml) and acidified with concentrated hydrochloric acid. The solid material is collected by filtration, washed with water and dried yielding white crystals, 1.3 g (85%), mp 186–188° C.

4C 5-Bromo-6-chloro-2-methoxybenzoyl chloride

A mixture of 4B (1.2 g, 4.6 mmol), dichloromethane (15 ml) and oxalyl chloride (1 ml) is stirred at room temperature for 2 hours. The mixture is concentrated and the resulting benzoylchloride is used without further purification.

4D 5-bromo-6-chloro-6'-methyl-2,2'3',4'-tetramethoxy-benzophenone

A mixture of 3,4,5-trimethoxytoluene (0.83 g; 4.6 mmol), 4C (4.6 mmol), aluminium chloride (0.62 g, 4.6 mmol) and dichloromethane (20 ml) is stirred at room temperature for 3 hours. A mixture of water and ethyl acetate (1:1 v/v; 50 ml) is then added. The organic phase is concentrated and the residue is crystallized from diisopropylether and recrystallized from methanol. The solid material is collected by vacuum filtration, washed with water and dried yielding yellow crystals, 0.7 g, (35.4% y) mp 87–88° C.

EXAMPLE 5

Preparation of 1-(6'-methyl-2',3',4'-trimethoxybenzoyl)-2-methoxynaphthalene

5A Methyl (2-methoxynaphth-1-yl)-carboxylate

A mixture of 2-hydroxynaphth-1-ylcarboxylic acid (18.82 g, 100 mmol), sodium hydroxide (8.8 g, 220 mmol), dimethylsulfate (31.5 g, 250 mmol) and water (200 ml) is heated to 70° C. with stirring for 20 hours. Subsequently, the reaction mixture is cooled to room temperature and extracted with ethyl acetate twice. The combined organic phases are concentrated and the residue is used without further purification.

5B Methyl (2-methoxynaphth-1-yl)-carboxylic acid

A mixture of crude 5A (10.5 g, 48 mmol), water (100 ml), methanol (150 ml) and sodium hydroxide (12 g, 300 mmol) is heated under reflux with stirring. The reaction mixture is extracted with diethylether twice. The aqueous reaction mixture is filtered and acidified with concentrated hydrochloric acid. The solid material is collected by filtration, washed with water and dried yielding yellow crystals, 9.45 g (97.4%), mp 175–176° C.

5C 1-(6'-methyl-2',3',4'-trimethoxybenzoyl)-2-methoxynaphthalene

A mixture of 5B (2.02 g, 10 mmol), 3,4,5-trimethoxytoluene (1.82 g; 10 mmol), P$_2$O$_5$ (10.0 g) and dichloromethane is stirred at room temperature for 16 hours. Subsequently, the dichloromethane is distilled off and the residue is diluted with ethyl acetate. The organic phase is washed with water and concentrated. The residue is purified by column chromatography (petrol ethers:ethyl acetate, 8:2 v/v) and recrystallized from petrol ether: diisopropylether (1:1 v/v). The solid material is collected by vacuum filtration, washed with cold petrol ether: diisopropylether (1:1 v/v) and dried, yielding white crystals, 0.9 g, (24.6%) mp 72° C.

EXAMPLE 6

Preparation of 5-bromo-6.6'-dimethyl-2,2'3',4'-tetramethoxy-benzophenone

6A Ethyl 5-bromo-6-methyl-2-methoxybenzoate

A mixture of ethyl 6-methyl-2-methoxybenzoate (8.4 g, 43.2 mmol), bromine (6.9 g, 43.2 mmol) and tetrachloromethane (170 ml) is stirred at room temperature for 60 hours. The reaction mixture is poured into water and extracted with ethyl acetate. The organic phase is separated and concentrated. The crude product is obtained as a yellow oil, 10.3 g (87% y) and is used without further purification.

6B 5-Bromo-6-methyl-2-methoxybenzoic acid

A mixture of 6A (9.8 g, 34.1 mmol), water (40 ml), ethanol (80 ml) and sodium hydroxide (2.7 g, 68.3 mmol) is heated under reflux with stirring for 42 hours. The reaction mixture is diluted with water (80 ml), acidified with concentrated hydrochloric acid and extracted with dichloromethane. The organic phase is separated and concentrated. The solid material is collected by filtration, washed with water and dried yielding off-white crystals, 5.4 g (61%), mp 81–83° C.

6C 5-bromo-6,6'-dimethyl-2,2'3',4'-tetramethoxy-benzophenone

A mixture of 6B (24 g, 10 mmol), 3,4,5-trimethoxytoluene (1.82 g; 10 mmol), P$_2$O$_5$ (10.0 g) and dichloromethane (150 ml) is stirred at room temperature for 16 hours. Subsequently, the dichloromethane is distilled off and the residue is diluted with ethyl acetate. The organic phase is washed with water and concentrated. The residue is purified by column chromatography (petrol ether: ethyl acetate, 8:2 v/v) and recrystallized from diisopropylether. The solid material is collected by vacuum filtration, washed with cold petrol ethers:diisopropylether (1:1 v/v) and dried, yielding white crystals, 2.2 g (54% ), mp 89–91° C.

EXAMPLES 7–49

Using essentially the same procedures described hereinabove for Examples 1 to 6 and employing standard derivatization techniques where appropriate, the following compounds are prepared and shown in Tables I and II:

TABLE I

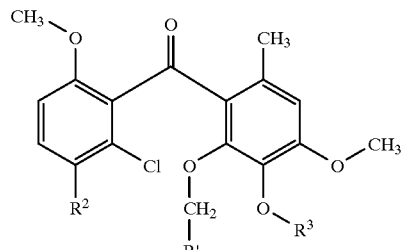

| Example | R' | R$^2$ | R$^3$ | Melting point (° C.) |
|---|---|---|---|---|
| 7 | H | methyl | methyl | 95 |
| 8 | n-propyl | methyl | methyl | oil |
| 9 | n-butyl | methyl | methyl | oil |
| 10 | H | H | methyl | 51 |
| 11 | n-propyl | H | methyl | oil |
| 12 | 2-methylpropyl | H | methyl | 55–56 |
| 13 | phenyl | H | methyl | 120–122 |
| 14 | 4-fluorophenyl | H | methyl | 96–98 |
| 15 | 4-methylphenyl | H | methyl | 80 |
| 16 | 3-methylphenyl | H | methyl | oil |
| 17 | 2-fluorophenyl | H | methyl | 90–93 |
| 18 | 2-methylpropyl | methyl | methyl | |
| 19 | phenyl | methyl | methyl | |
| 20 | 4-fluorophenyl | methyl | methyl | |
| 21 | 4-methylphenyl | methyl | methyl | |
| 22 | 3-methylphenyl | methyl | methyl | |
| 23 | 2-fluorophenyl | methyl | methyl | |
| 24 | n-propyl | Br | methyl | |
| 25 | n-butyl | Br | methyl | |
| 26 | 2-methylpropyl | Br | methyl | |
| 27 | phenyl | Br | methyl | |
| 28 | 4-fluorophenyl | Br | methyl | |
| 29 | 4-methylphenyl | Br | methyl | |
| 30 | 3-methylphenyl | Br | methyl | |
| 31 | 2-fluorophenyl | Br | methyl | |
| 32 | n-propyl | H | n-butyl | oil |
| 33 | H | methyl | CO-ethyl | |
| 34 | H | methyl | H | |
| 35 | H | methyl | n-propyl | oil |
| 36 | H | methyl | n-butyl | oil |
| 37 | H | methyl | n-pentyl | oil |
| 38 | H | methyl | 3-methyl-butyl | oil |
| 39 | H | NO$_2$ | methyl | oil |

TABLE II

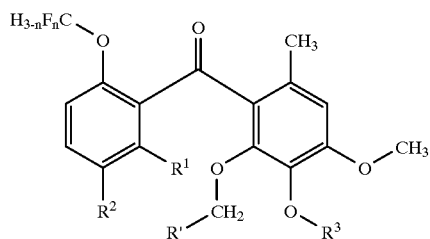

| Example | n | R¹ | R² | R' | R³ | Melting point (° C.) |
|---|---|---|---|---|---|---|
| 40 | 0 | methyl | Br | H | n-pentyl | oil |
| 41 | 0 | methyl | isopropyl | H | methyl | |
| 42 | 2 | Cl | H | H | methyl | oil |
| 43 | 2 | —CH=CH—CH=CH— | | H | methyl | oil |
| 44 | 0 | methyl | Br | n-propyl | methyl | |
| 45 | 0 | methyl | Cl | H | methyl | |
| 46 | 0 | methyl | I | H | methyl | 102 |
| 47 | 0 | methyl | Br | methyl | methyl | |
| 48 | 0 | methyl | NO₂ | H | methyl | 77 |
| 49 | 0 | methyl | methoxy | H | methyl | 135–137 |

Biological Investigations

A Foliar Systemicity

Wheat Powdery Mildew (WPM):

HOST: Wheat (*Triticum aestivum* L.) variety Kanzler

PATHOGEN: *Erysiphe graminis* DC. f.sp. *tritici* E. Marchal

TEST PROCEDURE:

1. Wheat seed (8/pot) is planted in 8 cm diameter plastic pots in the greenhouse.
2. When the primary leaf is fully expanded, the plants are cut back to four in each pot of which two are marked with a permanent marker 5 cm below the leaf tip on the upper leaf surface. Thus there are two band-treated and two untreated plants in each pot.
3. A pipette is used to apply 5 μl of the formulated compound in a band on the lower leaf surface opposite the mark. The application band should cover the whole leaf width. After application, the plants are not moved until the bands are dry (half an hour or so later).
4. After treated plants have dried, they are moved to the greenhouse and kept there for 2 days to allow for movement of the compounds. The plants are maintained with bottom watering.
5. Two days after application, the plants are inoculated by dusting them with powdery mildew conidia in the greenhouse. Evaluations are typically made 7–8 days after inoculation.

Evaluation

Three types of compound movement are assessed by evaluating disease in three areas of each band-treated leaf.

Translaminar movement: The percent disease area is assessed for the translaminar band area (marked area of the upper leaf surface directly opposite where band was applied on the lower leaf surface; width of band approximately 5 mm). Translaminar disease control is then calculated using the following formula:

$$\% \text{ disease control} = 100 - \frac{\% \text{ disease in treated plants}}{\% \text{ disease in untreated plants}} \times 100$$

Distal movement and proximal movement: The distal and proximal disease-free zones on the upper leaf surface are measured in mm. The distal direction is from the band toward the leaf apex and the proximal direction is from the band toward the leaf base. The percent of the disease-free zone relative to the entire distance between the band and leaf apex or base is calculated. If disease is noticeably lighter in the distal or proximal area this is also noted.

FORMULATION AND CONTROLS:

1. The compounds are formulated in a solvent/surfactant system consisting of 5% acetone and 0.05% Tween 20 in deionized water. Formulated compounds are prepared using deionized water. Compounds are typically tested at 400 ppm.
2. Two kinds of controls are included:
   Plants band-treated with the solvent/surfactant solution and inoculated (Solvent Blank).
   Untreated plants which are inoculated (Inoculated Control).

The results of this evaluation are shown in Table III:

TABLE III

| | Foliar Systemicity | | |
|---|---|---|---|
| Example No. | Proximal Movement (mm from band) | Distal Movement (mm from band) | Translaminar Activity (%) |
| 1 | 10 | 50 | 100 |
| 10 | 6 | 46 | 100 |
| Standard¹ | 4 | 5 | 100 |
| Standard² | 8 | 28 | 100 |

The following compounds, which are known from EP 0 727 141 have been used as standards:

Standard¹ 2,6-dichloro-6'-methyl-2',3',4'-trimethoxybenzophenone

Standard² 2',3',4'-trimethoxy-2,6,6'-trimethylbenzophenone

B-1 Comparison of the Fungicidal Activity of the 2-methoxy-benzophenones to a 2,6-dichloro- and 2,6-dimethyl-benzophenone Test diseases:

(a) Wheat Powdery Mildew (WPM):

HOST: Wheat (*Triticum aestivum* L.) variety Kanzler

PATHOGEN: *Erysiphe graminis* DC. f.sp. *tritici* E. Marchal (b) Barley Powdery Mildew (BPM):

HOST: Barley (*Hordeum vulgare* L.) variety Golden Promise

PATHOGEN: *Erysiphe graminis* DC. f.sp. *hordei* E. Marchal

TEST PROCEDURE:

This test is a zero day protectant test for control of wheat and barley powdery mildews.
1. Wheat or barley seed (approximately 8–10/pot) is planted in 6 cm diameter plastic pots and maintained in the greenhouse.
2. When the primary leaf is fully expanded, formulated test compounds are sprayed with a single nozzle overhead track sprayer at a rate of 200 l/ha.
   Plants are then allowed to air-dry.
3. Inoculation follows about three hours after compound application. Plants are set up on greenhouse benches with bottom watering mats and inoculated by dusting them with conidia from powdery mildew infected plants (stock cultures at an age of 10–14 days).
4. Disease on the primary leaf as percent leaf area with disease symptoms/signs is evaluated about 7 days after inoculation. The tips and bases of the leaves are excluded from the evaluation.

Percent disease control is then calculated by the following formula:

$$\% \text{ disease control} = 100 - \frac{\% \text{ infection in treated plants}}{\% \text{ infection in untreated plants}} \times 100$$

FORMULATION, REFERENCE COMPOUNDS AND CONTROLS:
1. Technical compounds are formulated in a solvent/surfactant system consisting of 5% acetone and 0.05% Tween 20 in deionized water. Compounds are dissolved in acetone prior to addition of the water; the Tween 20 can be added through either the acetone or the water. Dilutions are made using the solvent/surfactant system. Test compounds are typically tested over a range of concentrations covering several orders of magnitude and then ED values are calculated for comparison of compounds.
   Formulated compounds are prepared using deionized water.
2. Two kinds of controls are included:
   Plants treated with the solvent/surfactant solution and inoculated (Solvent Blank).
   Untreated plants which are inoculated (Inoculated Control).

The results of this evaluation are shown in Table IV:

TABLE IV

Fungicidal activity of 2-methoxybenzophenones (ED90 values)
Comparison of the fungicidal activity of the 2-methoxy-benzophenones to a 2,6-dichloro-
and 2,6-dimethyl benzophenone
Results are from 0 day protectant tests in which all analogs were tested side-by-side.

| | | | ED9O (ppm) | | | | | | |
|---|---|---|---|---|---|---|---|---|---|
| Di-sease | Standard[1] | Standard[2] | 2-methoxy Benzophenone Example | | | | | | Reference Quinoxy-fen |
| | | | 1 | 4 | 6 | 7 | 10 | 45 | |
| WPM | 28 | 20 | 4 | 5 | 0.1 | 7 | 7 | 0.1 | 12 |
| BPM | 24 | 8 | 6 | 7 | 0.9 | 6 | 8 | <0.1 | 27 |

Compounds applied as technical material formulated in 0.5% acetone 0.05% Tween 20 water B-2 Comparison of the Curative and Residual Fungicidal Activity of the 2-methoxy-benzophenones to a 2,6-dichloro- and 2,6-dimethyl-benzophenone Test diseases:
(a) Wheat Powdery Mildew (WPM):
HOST: Wheat (*Triticum aestivum* L.) variety Kanzler
PATHOGEN: *Erysiphe graminis* DC. f.sp. *tritici* E. Marchal
(b) Cucumber Powdery Mildew (QPM):
HOST: Cucumber (*Cucumis sativus* L.) variety Bush pickle
PATHOGEN: *Erysiphe cichoracearum* DC

TEST PROCEDURE:

This test procedure is for curative and residual control of powdery mildew diseases.
1. Wheat seed (approximately 8–10/pot) or cucumber seed (1 seed/pot) is planted in 6 cm diameter plastic pots and maintained in the greenhouse.
2. When the primary leaf (wheat) or the cotyledons (cucumber) is/are fully expanded, formulated test compounds are sprayed with a single nozzle overhead track sprayer at a rate of 200 l/ha.
   Plants are then allowed to air-dry.
3. Inoculation precedes treatment by 2 days in the case of curative evaluations and follows treatment by 3 days in case of residual evaluations. For inoculation, plants are set up on greenhouse benches with bottom watering mats and inoculated by dusting them with conidia from powdery mildew infected plants (stock cultures at an age of 10–14 days). Between inoculation and treatment for curative evaluations and between treatment and inoculation for residual evaluations, plants are maintained in the greenhouse with bottom watering.
4. Disease on the primary leaf (wheat) or on the cotyledons (cucumber) as percent leaf area with disease symptoms/signs is evaluated about 7 days after inoculation. In the case of wheat, the tips and bases of the leaves are excluded from the evaluation.

Percent disease control is then calculated by the following formula:

$$\% \text{ disease control} = 100 - \frac{\% \text{ infection in treated plants}}{\% \text{ infection in untreated plants}} \times 100$$

FORMULATION, REFERENCE COMPOUNDS AND CONTROLS:
1. Technical compounds are formulated in a solvent/surfactant system consisting of 5% acetone and 0.05% Tween 20 in deionized water. Compounds are dissolved in acetone prior to addition of the water; the Tween 20 can be added through either the acetone or the water. Dilutions are made using the solvent/surfactant system. Formulated compounds are prepared using deionized water.
2. Two kinds of controls are included:
   Plants treated with the solvent/surfactant solution and inoculated (Solvent Blank).
   Untreated plants which are inoculated (Inoculated Control).

The results of this evaluation are shown in Table V:

TABLE V

Curative and Residual Fungicidal activity of 2-methoxy-benzophenones

| | | | | Disease control (% efficacy) | | | |
|---|---|---|---|---|---|---|---|
| Disease Test | Rate (ppm) Test | Stan-dard[1] A | Stan-dard[2] B | 2-methoxy Benzophenone Example | | | |
| | | | | 1 A/B | 6 A/B | 4 B | 7 C |
| WPM 2 da C | 1250 | 79 | 92 | 88/85 | 98/87 | 61 | 97 |
| | 125 | 60 | 74 | 79/65 | 95/89 | 71 | 93 |
| | 12,5 | 31 | 55 | 69/52 | 90/61 | 55 | 73 |
| WPM | 1250 | 100 | 100 | 100/100 | 100/100 | 100 | 100 |

TABLE V-continued

Curative and Residual Fungicidal activity of 2-methoxy-benzophenones

| | | | | Disease control (% efficacy) | | | |
|---|---|---|---|---|---|---|---|
| | Rate | Stan- | Stan- | 2-methoxy Benzophenone Example | | | |
| Disease Test | (ppm) Test | dard[1] A | dard[2] B | 1 A/B | 6 A/B | 4 B | 7 C |
| 3 da R | 125 | 83 | 81 | 100/100 | 100/100 | 100 | 100 |
| | 12,5 | 75 | 70 | 90/100 | 100/100 | 99 | 99 |
| QPM | 1250 | 100 | 89 | 100/100 | 100/100 | 100 | 100 |
| 3 da R | 125 | 0 | 6 | 5/61 | 92/92 | 97 | 89 |
| | 12,5 | 0 | 14 | 2/3 | 2/35 | 8 | 2 |

2 da C = 2 day curative Inoculation 2 days BEFORE application
3 da R = 3 day residual Inoculation 3 days AFTER application

What is claimed is:

1. A compound of formula I:

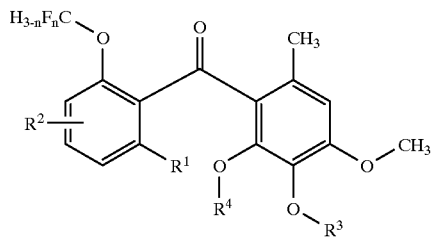

(I)

wherein
R[1] represents a halogen atom or an alkyl group;
R[2] represents a hydrogen or halogen atom, or an alkyl, alkoxy or nitro group; or R[1] and R[2] together represent a group of formula —CH=CH—CH=CH—;
R[3] and R[4] each independently represent an optionally substituted alkyl or benzyl group; and
n is an integer from 0 to 3.

2. A compound as claimed in claim 1, wherein
R[1] represents a chloro atom or a methyl group;
R[2] represents a hydrogen, chloro or bromo atom;
R[3] represents a $C_{1-5}$ alkyl group;
R[4] represents a $C_{1-5}$ alkyl group or benzyl group, being optionally substituted by at least halogen atom, or $C_{1-4}$ alkyl or alkoxy group; and
n is 0.

3. A compound as claimed in claim 2 being selected from the group consisting of
6,6'-dimethyl-2,2',3',4'-tetramethoxy-benzophenone,
6,6'-dimethyl-3'-pentoxy-2,2',4'-trimethoxy-benzophenone,
5-bromo-6,6'-dimethyl-2,2',3',4'-tetramethoxy-benzophenone,
5-chloro-6,6'-dimethyl-2,2',3',4'-tetramethoxy-benzophenone,
5-iodo-6,6'-dimethyl-2,2',3',4'-tetramethoxy-benzophenone,
6-chloro-6'-methyl-2,2',3',4'-tetramethoxy-benzophenone,
5-bromo-6-chloro-6'-methyl-2,2',3',4'-tetramethoxy-benzophenone,
6-chloro-5,6'-dimethyl-2,2',3',4'-tetramethoxy-benzophenone,
2'-butoxy-6-chloro-6'-methyl-2,3',4'-trimethoxy-benzophenone,
2'-butoxy-6-chloro-5,6'-dimethyl-2,2',3'-trimethoxy-benzophenone
6-chloro-2'-(2-fluorobenzyloxy)-6'-methyl-2,3',4'-trimethoxy-benzophenone,
6-chloro-2'-(4-fluorobenzyloxy)-6'-methyl-2,3',4'-trimethoxy-benzophenone,
5-bromo-6,6'-dimethyl-3'-pentyloxy-2,2',4'-trimethoxy-benzophenone
6-chloro-6'-methyl-2'-pentyloxy-2,3',4'-trimethoxy-benzophenone,
6-chloro-2'-(3-methylbutyloxy)-6'-methyl-2,3',4'-trimethoxy-benzophenone,
2'-benzyloxy-6-chloro-6'-methyl-2,3',4'-trimethoxy-benzophenone,
6-chloro-2'-(3-methylbenzyloxy)-6'-methyl-2,3',4'-trimethoxy-benzophenone,
6-chloro-2'-(4-methylbenzyloxy)-6'-methyl-2,3',4'-trimethoxy-benzophenone,
6-chloro-2-difluoromethoxy-6'-methyl-2',3',4'-trimethoxy-benzophenone,
1-(6'-methyl-2',3',4'-trimethoxybenzoyl)-2-methoxynaphthalene, and
1-(6'-methyl-,2',3',4'-trimethoxybenzoyl)-2-difluoromethoxynaphthalene.

4. A composition which comprises a fungicidally effective amount of at least one compound of claim 1, and a carrier.

5. A method of combating fungus or a fungal plant disease at a locus, which comprises treating the locus with a compound of claim 1.

6. A method of combating fungus or a fungal plant disease at a locus, which comprises treating the locus with the composition of claim 4.

7. The method of claim 5 wherein the fungal plant disease is caused by ascomycetes.

8. The method of claim 6 wherein the fungal plant disease is caused by ascomycetes.

9. The method according to claim 5 wherein the fungus is a member of the subgroup Erysiphales.

10. The method of claim 9 wherein the fungus is selected from *Erysiphe graminis, Erysiphe cichoracearum, Podosphaera leucotricha* or *Uncinula necator*.

11. The method according to claim 6 wherein the fungus is a member of the subgroup Erysiphales.

12. The method of claim 11 wherein the fungus is selected from *Ersiphe graminis, Erysiphe cichoracearum, Podosphaera leucotricha* or *Uncinula necator*.

13. A compound of formula IA:

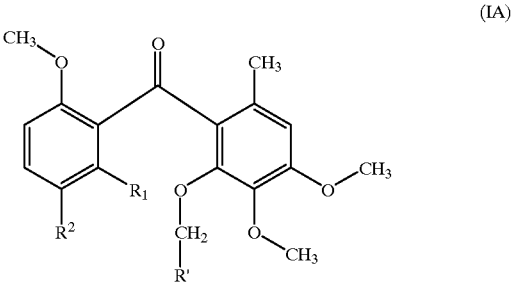

(IA)

in which $R^1$ represents a chloro atom or a methyl group, $R^2$ represents a hydrogen, chloro or bromo atom or a methyl group, and R' represents a hydrogen atom or a $C_{1-4}$alkyl or a phenyl group being optionally substituted by one or more fluorine atoms or one or more $C_{1-4}$alkyl groups.

* * * * *